Figure 1:
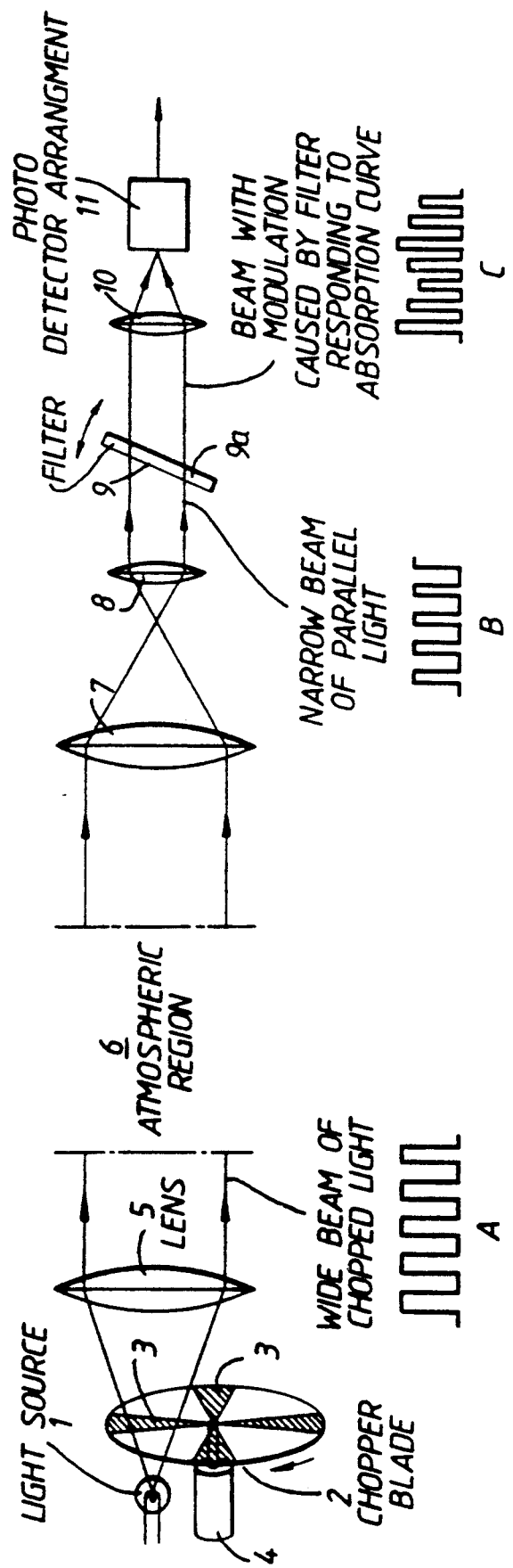

United States Patent [19]

Goody

[11] Patent Number: 5,268,745
[45] Date of Patent: Dec. 7, 1993

[54] LIGHT RADIATION ABSORPTION GAS DETECTOR

[75] Inventor: Brian A. Goody, Carshalton, Great Britain

[73] Assignee: Siemens Plessey Controls Limited, Poole, England

[21] Appl. No.: 873,951

[22] Filed: Apr. 24, 1992

[30] Foreign Application Priority Data

Apr. 26, 1991 [GB] United Kingdom ............... 9108978
Jul. 10, 1991 [GB] United Kingdom ............... 9114910

[51] Int. Cl.⁵ .......................................... G01N 21/27
[52] U.S. Cl. ................................. 356/418; 356/419; 356/51; 250/339; 250/343
[58] Field of Search ............. 356/51, 409, 414, 418, 356/419; 250/338.5, 339, 343

[56] References Cited

U.S. PATENT DOCUMENTS

| | | | |
|---|---|---|---|
| 2,834,246 | 5/1958 | Foskett et al. | 356/418 |
| 3,877,812 | 4/1975 | Thompson | 356/51 |
| 4,167,338 | 9/1979 | Kraus | 356/418 |

FOREIGN PATENT DOCUMENTS 1583845 2/1981 United Kingdom .
2163251A 2/1986 United Kingdom .

Primary Examiner—F. L. Evans
Attorney, Agent, or Firm—Keck, Mahin & Cate

[57] ABSTRACT

A light radiation absorption gas detector for detecting the presence of a specified gas, comprising a light source, a region containing a gas to be detected through which light from the source is passed, an interference filter having a substantially flat face and a light radiation absorption peak at a wavelength which facilitates detection of the specified gas, a shaft to which the filter is by means of arms secured for rotation so that a perpendicular to the flat face of the filter is at an angle to the axis of the rotation and light detector means responsive to light from the source which has passed through the region and the filter, for detecting predetermined light amplitude variations, wherein light from the source is arranged to be projected towards the filter at an angle offset from the axis of shaft rotation whereby a filter pass band which includes the said wavelength is scanned consequent upon rotation of the filter, thereby to produce amplitude variations of light in the presence within the region of the specified gas, whereby detection of the specified gas by the detector means is facilitated.

10 Claims, 3 Drawing Sheets

LIGHT RADIATION ABSORPTION GAS DETECTOR

This invention relates to gas detectors and more especially it relates to light radiation absorption gas detectors for detecting the presence of a specified gas or gases.

Such gas detectors make use of the fact that gases absorb more light at some wavelengths than others, each gas having its own unique absorption peak or peaks.

Such detectors are well known and comprise an interference filter which is chosen to pass light in a pass band including a wavelength corresponding to an absorption peak for a gas to be detected and having the characteristic that the pass band is dependent upon the angle at which light is incident on the filter.

Thus by changing the angle of incidence, the said pass band, or part thereof, can be scanned correspondingly is the angle is changed, such that detection of an absorption peak indicative of the presence of a particular gas as facilitated.

Interference filters comprise a film or films of predetermined thickness carried on a transparent substrate, the thickness of the film or films being chosen to afford a required filter characteristic. The construction and manufacture of such filters is well known and will therefore not be further described herein.

In order to change the angle of incidence to produce a required scanning function, it is known to mount the filter on an oscillating shaft. This known arrangement is inefficient due to the need for repeated reversal of shaft direction, with consequent changing inertial forces, which is obviously wasteful of energy. Moreover, the amplitude of the oscillatory motion may tend to vary with temperature and thus temperature stability of the gas detector is adversely affected.

It is an object of the present invention to provide a light radiation absorption gas detector in which the aforementioned disadvantages are obviated at least in part.

According to the present invention a light radiation absorption gas detector for detecting the presence of a specified gas, comprises a light source, a region containing a gas to be detected through which light from the source is passed, an interference filter having a substantially flat face and a light radiation absorption peak at a wavelength which facilitates detection of the specified gas, a shaft to which the filter is secured for rotation so that a perpendicular to the flat face of the filter is at an angle to the axis of the rotation and light detector means responsive to light from the source which has passed through the region and the filter, for detecting predetermined light amplitude variations, wherein light from the source is arranged to be projected towards the filter at an angle offset from the axis of shaft rotation whereby a filter pass band which includes the said wavelength is scanned consequent upon rotation of the filter, thereby to produce amplitude variations of light in the presence within the region of the specified gas, whereby detection of the specified gas by the detector means is facilitated.

By arranging that the filter is secured to the shaft so that a perpendicular to its flat face is arranged at an angle to the axis of rotation, and by further arranging that light is projected towards the filter at an angle offset from the shaft axis, it will be apparent that light from the source will strike the filter at an angle which changes with shaft rotation whereby a scanning function of the filter pass band is effected.

By using an arrangement according to the present invention, the shaft may be rotated at a substantially constant angular velocity whereby changing inertial forces (as produced by oscillatory systems) with their attendant disadvantages, are not present.

Figure 2:
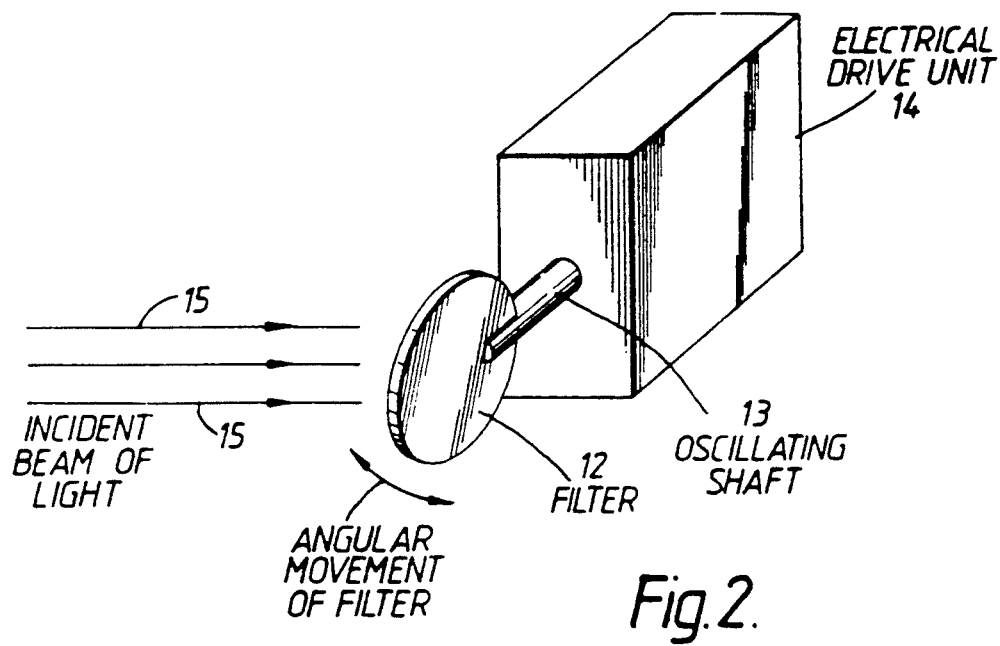
Figure 3:
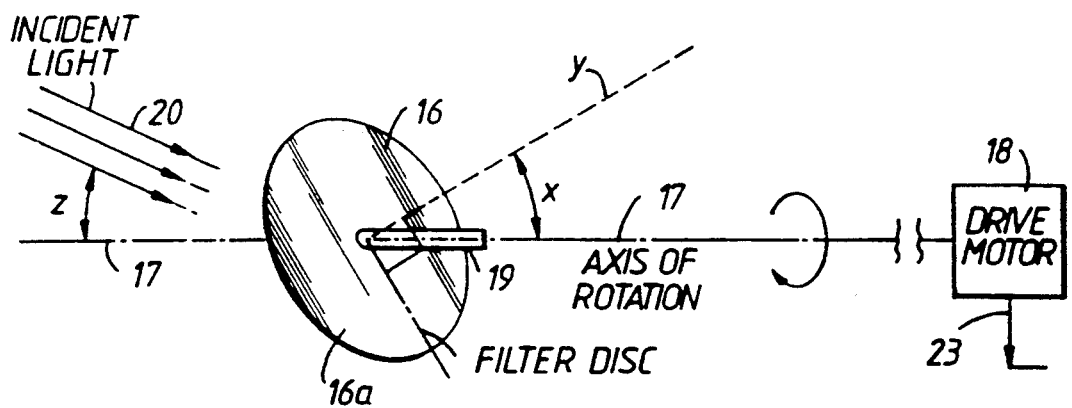
Figure 4:
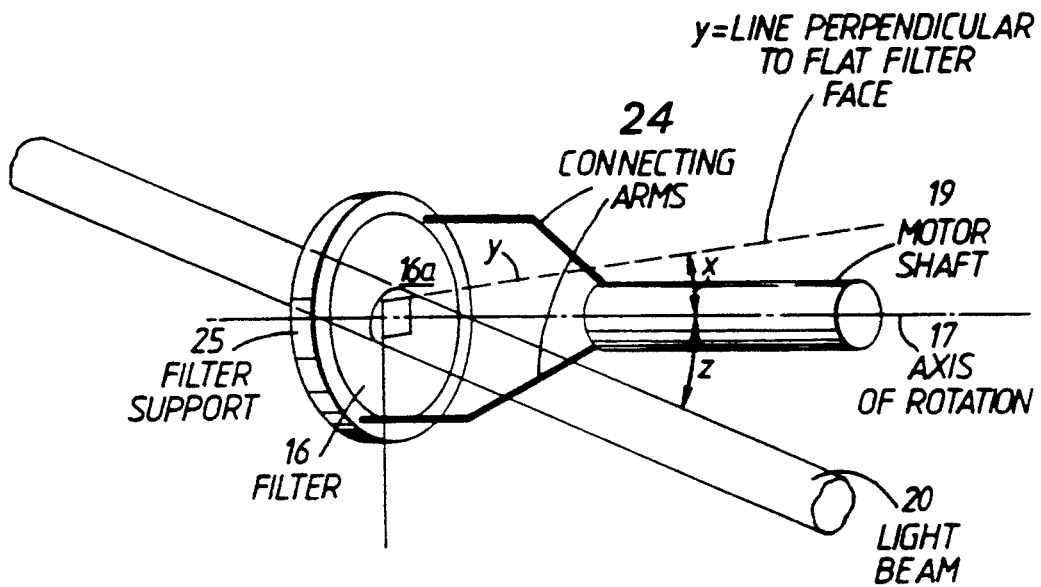
Figure 5:
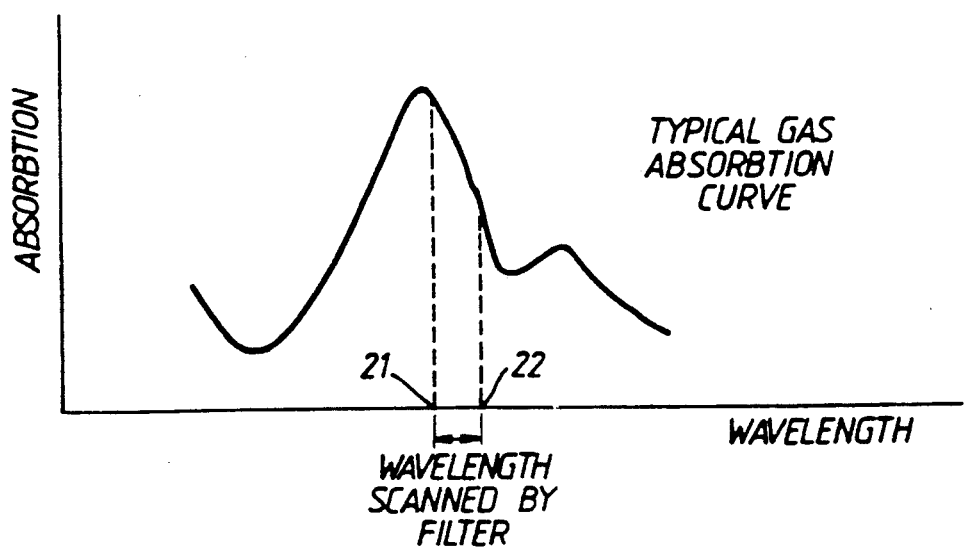

One embodiment of invention will now be described by way of example with reference to the accompanying drawings in which:

FIG. 1 is a generally schematic block diagram of a light absorption gas detector, FIG. 2 is a somewhat schematic perspective view of a known filter arrangement for use with the system shown in FIG. 1, FIG. 3 is a somewhat schematic perspective view of a filter arrangement for use in a gas detector as shown in FIG. 1 and according to one embodiment of the present invention, FIG. 4 is a somewhat schematic perspective view of an alternative filter arrangement for use in a gas detector as shown in FIG. 1 and according to an alternative embodiment of the present invention wherein parts corresponding to those shown in FIG. 3 bear the same numerical designations, and FIG. 5 is a graph showing a typical gas absorption curve.

Referring now to FIG. 1, a light absorption gas detector comprises a light source 1 which in the present example is a filament lamp. Light from the source is directed towards an optical chopper 2 having blades 3 which are rotated by means of a motor 4. Light from the chopper 2 is passed via a lens 5 through a gas sensing region 6. Due to operation of the chopper 2, light in the region 6 comprises pulses as shown in waveform A. The light pulses are fed through an optical system comprising lenses 7 and 8 to produce a narrow beam of parallel light pulses as shown in waveform B, which corresponds substantially with waveform A. Light from the lens 8 is fed through a filter assembly 9 which comprises an interference filter 9a having a pass band including a wavelength which corresponds to the absorption wavelength of a gas to be detected.

The operation and construction of the filter assembly will hereinafter be described in more detail with reference to FIGS. 2, 3 4 and 5. Light from the filter 9a is fed through a lens 10 to a photo detector arrangement 11, which includes a light detector element and a signal processor.

If a gas to be detected is present in the region 6, absorption occurs which results in a modulation being imposed on the waveform shown in waveform B (produced by movement of the filter element 9a as will hereinafter be explained), so as to produce a modulated waveform C.

Referring now to FIG. 2, the filter in one known arrangement comprises an interference filter element 12 which is attached to a shaft 13. The shaft 13 is coupled to an electrical drive unit 14 which produces oscillatory angular movement of the shaft 13. The electrical drive unit 14 may be a galvanometer movement for example. Thus it will be appreciated that light projected towards the filter 12 in the direction of arrows 15 will be incident upon the filter at an angle which is varied as the shaft 13 oscillates. As the angle of incidence changes consequent upon oscillation of the shaft 13, a pass band including the wavelength of absorption of a gas to be detected is scanned. The filter is chosen to include an absorption wavelength of a gas to be detected and thus the filter 12 would be chosen in accordance with the type of gas to be detected. This known arrangement as shown in FIG. 2 has several disadvantages as hereinbefore explained, which stem from the fact that the filter 12 and the shaft are oscillated.

In order to avoid these disadvantages, a filter arrangement as shown in FIG. 3 may be used. The filter arrangement comprises a filter element 16 which is secured to a shaft 19 having an axis of rotation 17. The shaft 19 is driven by a motor 18 shown schematically. The filter element 16, which comprises a substantially flat circular disk, is secured to the shaft 19 so that a perpendicular y to its flat face 16a is set at an angle x with respect to the axis of rotation 17. Light incident on the filter element 16, which is projected from the lens 8 as shown in FIG. 1, is arranged to be offset by an angle z with respect to the axis of rotation 17. Although in the arrangement of FIG. 3 the filter element 16 is shown attached centrally to the shaft 19, in an alternative arrangement the filter element 16 may be supported at its circular peripheral edge by an angular rim or bezel 25 which is coupled to a pair of support arms 24 as shown in FIG. 4 which are coupled to the shaft 19. With this arrangement it can be arranged that light projected through the filter element 16 is not obstructed by the shaft 19.

Preferably an even number of connecting arms 24 are used, (two are shown in FIG. 4) symmetrically spaced around the bezel 25. This ensures that with two arms, any interruption of the beam by the arms 24 will be at twice the oscillation frequency and may hence be easily rejected by the electronics processing. This however is not an essential requirement if the chopper blade 2 shown in FIG. 1 is arranged to be correctly phased with the filter rotation such that the connecting arms break the light beam when the chopper interrupts the light.

A further advantage is obtained by arranging that the speed of rotation of the chopper blade is an even multiple of the speed of rotation of the filter. This tends to cancel errors caused by irregularities in the chopper blades as they similarly effect both positive and negative parts of the detected signal.

It is important that the portion of the Filter through which the light passes is substantially unchanged during the filter's rotation and the apparatus of FIG. 4 achieves this by using the central area of the Filter.

In operation of the gas detector, the filter element 16 is rotated at a substantially constant velocity by the motor 18 and it will be apparent that the angle of incidence of light rays 20 on the filter will vary as the element 16 rotates. If a gas is present in the region 6 as shown in FIG. 1, light modulation will be produced as shown in waveform C consequent upon rotation of the filter element 16.

Referring to FIG. 5, it will be appreciated that if a wavelength band between the points 21 and 22 on the horizontal axis of the curve is scanned, a light intensity variation will be produced which corresponds to the modulation as shown in waveform C, at a frequency which corresponds to the angular rotation rate of the shaft 19.

The filter will be chosen having regard to the gas to be detected and for the detection of methane for example, which has an absorption peak at 2.9 microns, a filter with a passband including 2.9 microns would be chosen and a wavelength band of between 2.8 microns to 2.9 microns would be scanned with the angles x and z being about 5 degrees and 30 degrees respectively. The detector arrangement 11 comprises a photo detector, (not shown), output signals from which are fed to a signal processor which serves for the identification of signal variations indicative of the presence of a specified gas.

It will be appreciated by those skilled in the art that any suitable form of detector arrangement 11 may be used and in order to facilitate detection of small signals, an output signal on a line 23 from the drive motor 18 may be provided which corresponds to the frequency of rotation whereby the detection of a corresponding modulation frequency as shown in the waveform C is facilitated.

Various modifications may be made to the arrangement described herein without departing from the scope of the invention and for example it will be appreciated that any suitable light source and filter may be used and for example an infra-red or an ultraviolet light source may be appropriate, together with a suitable filter, for the detection of some gases. It will also be appreciated that any means may be used to rotate the filter element 16 and that any suitable form of detection may be used to detect the resultant modulation of the signal produced in the presence of a gas in the region 6.

I claim:

1. A light radiation absorption gas detector for detecting the presence of a specified gas, comprising a light source, a region containing a gas to be detected through which a light beam from the source is passed, an interference filter having a substantially flat face and a light radiation absorption peak at a wavelength which facilitates detection of the specified gas, a shaft to which the filter is secured for rotation so that a perpendicular to the flat face of the filter is at an angle to the axis of the rotation, light detector means responsive to light from the source which has passed through the region and the filter for detecting predetermined light amplitude variations, and a light chopper or interrupter interposed between said source and said light detector means, wherein light from the source is directed via first lens means through the region, via second lens means from the region to the filter and via third lens means from the filter to the light detector means, and wherein light from the source is arranged to be projected towards the filter at an angle offset from the axis of shaft rotation whereby a filter pass band which includes the said wavelength is scanned consequent upon rotation of the filter, thereby to produce amplitude variations of light in the presence within the region of the specified gas, whereby detection of the specified gas by the detector means is facilitated.

2. A gas detector as claimed in claim 1, wherein the light chopper is interposed between the light source and the first lens means.

3. A gas detector as claimed in claim 1 wherein the filter is supported by arms which interrupt the light beam as the shaft is rotated.

4. A gas detector as claimed in claim 3 wherein the arms are positioned so as to interrupt the light beam synchronously with the chopper.

5. A gas detector as claimed in claim 3 wherein there are an even number of arms.

6. A gas detector as claimed in claim 1 wherein the chopper comprises rotary blades which interrupt the light beam at an even multiple of the shaft rotation rate.

7. A gas detector as claimed in claim 1, wherein the light detector means comprises an optical detector element effective to detect the light amplitude variations and a signal processor responsive to the said element for detecting electrical signal variations corresponding to the light amplitude variations produced in the presence within the region of the specified gas.

8. A gas detector as claimed in claim 7, wherein the signal processor is arranged to detect electrical signal variations in the form of amplitude modulation.

9. A gas detector as claimed in claim 1, further comprising a shaft rotating means comprising a motor.

10. A gas detector as claimed in claim 3, wherein the said filter is generally circular and supported at its circular peripheral edge by means of the arms.

* * * * *